US010012625B2

United States Patent
Lin et al.

(10) Patent No.: US 10,012,625 B2
(45) Date of Patent: Jul. 3, 2018

(54) RAMAN DETECTING CHIP FOR THIN LAYER CHROMATOGRAPHY AND METHOD FOR SEPARATING AND DETECTING AN ANALYTE

(71) Applicants: INDUSTRIAL TECHNOLOGY RESEARCH INSTITUTE, Hsinchu (TW); NATIONAL TSING HUA UNIVERSITY, Hsinchu (TW)

(72) Inventors: Ding-Zheng Lin, Taipei (TW); Ta-Jen Yen, Zhubei (TW); Bu-Shen Lee, New Taipei (TW); Chih-Hao Huang, Kaohsiung (TW)

(73) Assignees: INDUSTRIAL TECHNOLOGY RESEARCH INSTITUTE, Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/394,045

(22) Filed: Dec. 29, 2016

(65) Prior Publication Data
US 2017/0191938 A1  Jul. 6, 2017

Related U.S. Application Data

(60) Provisional application No. 62/274,938, filed on Jan. 5, 2016.

(30) Foreign Application Priority Data

Nov. 21, 2016 (TW) .............................. 105138051 A

(51) Int. Cl.
G01N 21/65 (2006.01)
G01N 30/92 (2006.01)
G01N 30/95 (2006.01)

(52) U.S. Cl.
CPC ........... G01N 30/92 (2013.01); G01N 21/658 (2013.01); G01N 30/95 (2013.01)

(58) Field of Classification Search
None
See application file for complete search history.

(56) References Cited

U.S. PATENT DOCUMENTS 7,158,219 B2  1/2007  Li et al.
7,400,395 B2  7/2008  Chan et al.
(Continued)

FOREIGN PATENT DOCUMENTS

CN  104422751 A  3/2015
CN  104897638 A  9/2015
(Continued)

OTHER PUBLICATIONS

Caudin, J.P., et al, "Coupling FT Raman and FT SERS microscopy with TLC plates for in situ identification of chemical compounds," Spectrochimica Acta Part A, 1995, vol. 51, pp. 1977-1983.
(Continued)

*Primary Examiner* — Shawn Decenzo
(74) *Attorney, Agent, or Firm* — Birch, Stewart, Kolasch & Birch, LLP

(57) ABSTRACT

A Raman detecting chip for thin layer chromatography and a method for separating and detecting an analyte are provided. The Raman detecting chip for thin layer chromatography includes a silicon substrate. The silicon substrate includes a flat portion and a plurality of silicon nanowires disposed on the flat portion, wherein each silicon nanowire has a top surface and a sidewall. A metal layer covers the top surface and at least a part of the sidewall. The silicon nanowire has a length from 5 μm to 15 μm.

11 Claims, 9 Drawing Sheets

(56) References Cited

U.S. PATENT DOCUMENTS

| | | |
|---|---|---|
| 7,738,096 B2 | 6/2010 | Zhao et al. |
| 7,880,876 B2 | 2/2011 | Zhao et al. |
| 7,940,387 B2 | 5/2011 | Dluhy et al. |
| 8,107,070 B2 | 1/2012 | Zhao et al. |
| 8,314,932 B2 | 11/2012 | Ou et al. |
| 8,358,407 B2 | 1/2013 | Hu et al. |
| 8,358,408 B2 | 1/2013 | Wu et al. |
| 8,547,549 B2 | 10/2013 | Kuo et al. |
| 8,687,186 B2 | 4/2014 | Wang et al. |
| 8,767,202 B2 | 7/2014 | Schmidt et al. |
| 8,810,789 B2 | 8/2014 | Zhao et al. |
| 8,898,811 B2 | 11/2014 | Jen et al. |
| 2011/0037976 A1 | 2/2011 | Zhao et al. |
| 2013/0128265 A1* | 5/2013 | Zhao ............... G01J 3/4412 356/301 |
| 2014/0125976 A1 | 5/2014 | Kim et al. |
| 2014/0218727 A1* | 8/2014 | Li ..................... G01N 21/658 356/301 |
| 2015/0050556 A1 | 2/2015 | Liu et al. |
| 2017/0212106 A1* | 7/2017 | Linke ............... G01N 33/54373 |

FOREIGN PATENT DOCUMENTS

| | | |
|---|---|---|
| TW | I485389 B | 5/2015 |
| WO | WO 2013/040782 A1 | 3/2013 |

OTHER PUBLICATIONS

Matejka, P., et al, "Near-Infrared Surface-Enhanced Raman Scattering Spectra of Heterocyclic and Aromatic Species Adsorbed on TLC Plates Activated with Silver," Applied Spectroscopy, 1996, vol. 50, No. 3, pp. 409-414.

Taiwanese Office Action for Appl. No. 105138051 dated Nov. 8, 2017.

Chang et al., "A Wafer-Scale Backplane-Assisted Resonating Nanoantenna Array SERS Device Created by Tunable Thermal Dewetting Nanofabrication," Nanotechnology, vol. 25, Mar. 14, 2014, pp. 1-9 (10 pages total).

Oh et al., "Glass Nanopillar Arrays with Nanogap-Rich Silver Nanoislands for Highly Intense Surface Enhanced Raman Scattering," Advanced Materials, vol. 24, 2012 (published online Mar. 27, 2012), pp. 2234-2237.

Seol et al., "A Nanoforest Structure for Practical Surface-Enhanced Raman Scattering Substrates," Nanotechnology, vol. 23, Feb. 6, 2012, pp. 1-7 (8 pages total).

Takei et al., "TLC-SERS Plates with a Built-In SERS Layer Consisting of Cap-Shaped Noble Metal Nanoparticles Intended for Environmental Monitoring and Food Safety Assurance," Journal of Nanomaterials, vol. 2015, Article ID 316189, 2015, pp. 1-9 (10 pages total).

Zhang et al., "Large-Area Silver-Coated Silicon Nanowire Arrays for Molecular Sensing Using Surface-Enhanced Raman Spectroscopy," Advanced Functional Materials, vol. 18, 2008, pp. 2348-2355.

Zhang et al., "Thin Layer Chromatography Coupled with Surface-Enhanced Raman Scattering as a Facile Method for On-Site Quantitative Monitoring of Chemical Reactions," Analytical Chemistry, vol. 86, Jun. 30, 2014, pp. 7286-7292.

* cited by examiner

RAMAN DETECTING CHIP FOR THIN LAYER CHROMATOGRAPHY AND METHOD FOR SEPARATING AND DETECTING AN ANALYTE

CROSS REFERENCE TO RELATED APPLICATIONS

This application claims the benefit of U.S. Provisional Application No. 62/274,938, filed on Jan. 5, 2016, which is incorporated herein by reference in its entirety.

The application is based on, and claims priority from, Taiwan Application Serial Number 105138051, filed on Nov. 21, 2016, the disclosure of which is hereby incorporated by reference herein in its entirety.

TECHNICAL FIELD

The technical field relates to a Raman detecting chip for thin layer chromatography and method for separating and detecting an analyte.

BACKGROUND

A Raman scattering spectrum has the advantages of fingerprint specificity and multi-domain applications, and thus it is widely applied in biological sensing, pharmaceutical, environmental monitoring, identification, and health monitoring. However, the detection sensitivity is low due to the weak Raman scattering signal strength and interference from other compounds when performing a qualitative and quantitative analysis utilizing the Raman spectroscopy.

Therefore, a novel detection system for extracting the Raman scattering signal and eliminating the interference signal is desired so as to address the aforementioned problems.

SUMMARY

Embodiments of the disclosure provide a Raman detecting chip for thin layer chromatography. The Raman detecting chip for thin layer chromatography of the disclosure includes a silicon substrate and a metal layer. The silicon substrate includes a planar portion and a plurality of silicon nanowires disposed on the flat portion, wherein each silicon nanowire has a top surface and a sidewall. The metal layer covers the top surface and at least a part of the sidewall of the silicon nanowire, wherein the silicon nanowire has a length from 5 µm to 15 µm Embodiments of the disclosure provide a method for separating and detecting an analyte. The method for separating and detecting an analyte of the disclosure includes providing the aforementioned Raman detecting chip for thin layer chromatography; providing a sample, wherein the sample comprises a solvent and at least one compound; spotting the sample on the aforementioned Raman detecting chip for thin layer chromatography; separating the sample by a thin layer chromatography process to obtain at least one analysis spot; and analyzing the analysis spot via surface enhanced Raman scattering spectroscopy.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
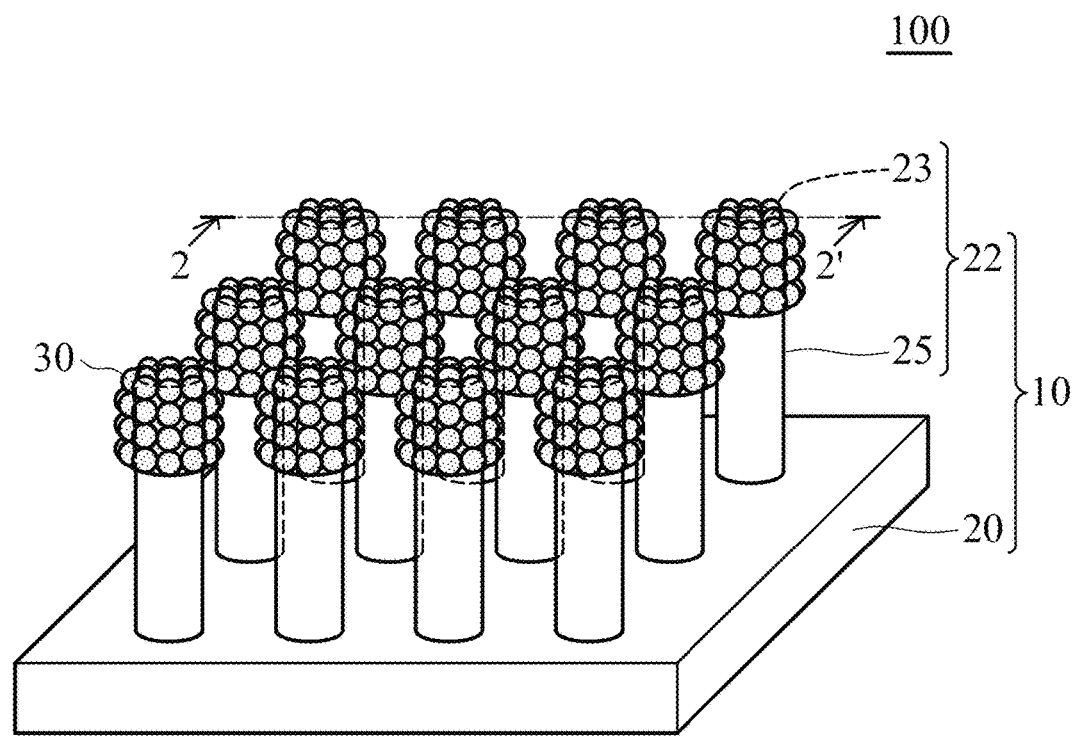
FIG. 1 is a schematic view of the Raman detecting chip for thin layer chromatography according to an embodiment of the disclosure.

The Raman detecting chip for thin layer chromatography and the method for separating and detecting an analyte of the disclosure are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments. In the drawings, the size, shape, or thickness of some of the elements may be exaggerated and not drawn in scale for illustrative purposes. The disclosure will be described with respect to particular embodiments and with reference to certain drawings but the disclosure is not limited thereto.

The disclosure provides a Raman detecting chip for thin layer chromatography and a method for separating and detecting an analyte. According to embodiments of the disclosure, the Raman detecting chip for thin layer chromatography can enable rapid separation and eliminate background interference due to the silicon nanowire having the specific length of the silicon substrate. In addition, the Raman signal detected by the Raman detecting chip of the disclosure can be enhanced due to the metal layer which covers a part of the surface of the silicon nanowire. As a result, the effects of the thin layer chromatography and surface enhanced Raman scattering spectroscopy can be achieved simultaneously, resulting in efficiently reducing background interference and increasing detectability.

FIG. 1 is a schematic view of the Raman detecting chip for thin layer chromatography according to an embodiment of the disclosure. The Raman detecting chip for thin layer chromatography 100 includes a silicon substrate 10, wherein the silicon substrate 10 consists of a planar portion 20 and a plurality of silicon nanowires 22 formed on the planar portion 20. Each silicon nanowire 22 can have a top surface 23 and a sidewall 25. A metal layer 30 can cover the top surface 23 and at least a part of the sidewall 25 of the silicon nanowire 22.

The metal layer can consist of a plurality of metal particles. According to embodiments of the disclosure, suitable materials of the metal particles can be silver, gold, aluminum, copper, tin, titanium, barium, platinum, cobalt, or a combination thereof. According to embodiments of the disclosure, the planar portion 20 and the plurality of silicon nanowires 22 of the silicon substrate 10 are integrally formed.

Figure 2:
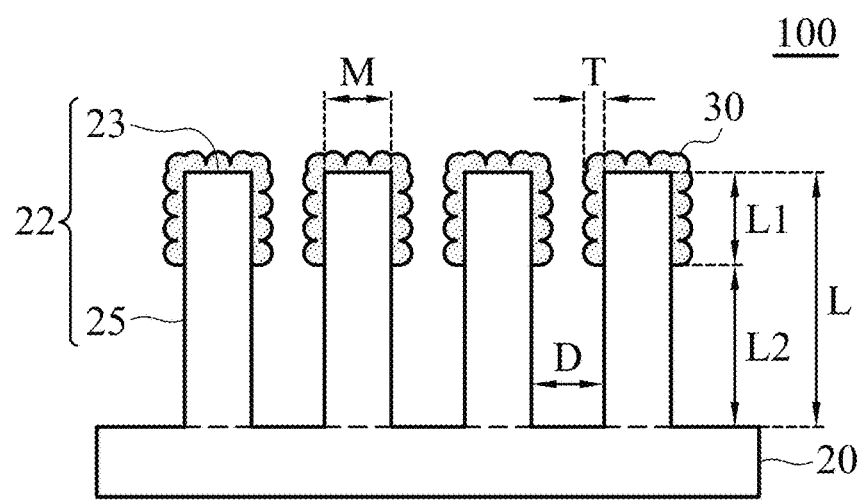
FIG. 2 is a cross-sectional view of the Raman detecting chip for thin layer chromatography as shown in FIG. 1 along the line 2-2'.

FIG. 2 is a cross-sectional view of the Raman detecting chip for thin layer chromatography as shown in FIG. 1 along the line 2-2'. As shown in FIG. 2, the silicon nanowire 22 can have a length L, wherein the length L can be from 5 μm to 15 μm (exhibiting the effects of thin layer chromatography). When the length L of the silicon nanowire 22 is too short, the adsorption force between the molecules of the analyte and the plurality of silicon nanowire 22 is greatly reduced, resulting in a longer separation distance, higher cost, and longer measurement time. Conversely, when the length L of the silicon nanowire 22 is too long, the adsorption force between the molecules of the analyte and the plurality of silicon nanowires 22 is greatly increased, resulting in the analyte not being able to be identified and isolated.

According to embodiments of the disclosure, as shown in FIG. 2, the top surface 23 of the silicon nanowire 22 can have a diameter M from about 50 nm to 200 nm. According to embodiments of the disclosure, a distance D between any two adjacent silicon nanowires (such as the distance between the side walls of any two adjacent silicon nanowires) is from about 50 nm to 200 nm. When the distance D is from about 100 nm to 200 nm, the short distance between the nano-particles of the metal layer disposed on the top surface of the two adjacent silicon nanowires may enhance the Raman scattering effect. Furthermore, the short distance can ensure that the adsorption force between the molecules of the analyte and the plurality of silicon nanowires 22 is sufficient. In addition, According to embodiments of the disclosure, the metal layer 30 can have a thickness T from about 20 nm to 100 nm. When the thickness T of the metal layer 30 is from about 20 nm to 100 nm, the short distance between the nano-particles of the metal layer disposed on the top surface of the two adjacent silicon nanowires may enhance the Raman scattering effect.

Figure 3:
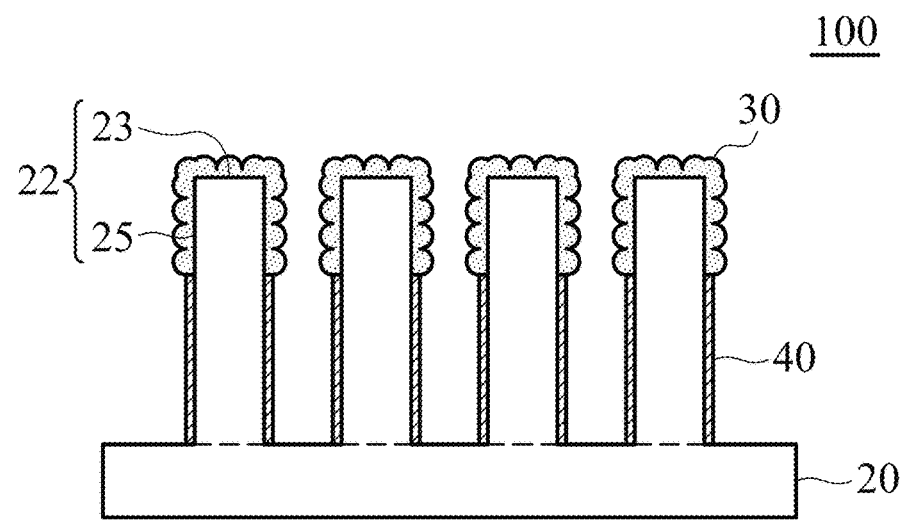
FIGS. 3-5 are cross-sectional views of the Raman detecting chips for thin layer chromatography according to other embodiments of the disclosure.

In addition, as shown in FIG. 2, the metal layer 30 completely covers top surface 23 of the nanowire 22, and further extends to the side wall 25 of the nanowire 22, such that the metal layer 30 covers a part of the side wall 25 of the silicon nanowire 22. As a result, a part of the side wall 25 of the silicon nanowire 22 is not covered by the metal layer 30. According to some embodiments of the disclosure, the ratio L1/L between the length L1 of the side wall covered by the metal layer 30 and the length L of the silicon nanowire 22 is from about 0.2 to 0.8. For example, the ratio L1/L between the length L1 of the side wall covered by the metal layer 30 and the length L of the silicon nanowire 22 can be from about 0.3 to 0.74. When the area of the silicon nanowire 22 covered by the metal layer 30 is too small (i.e. the ratio L1/L is too low), the enhanced Raman scattering effect would be confined to the superficial region of the silicon nanowire. Conversely, when the area of the silicon nanowire 22 covered by the metal layer 30 is too large (i.e. the ratio L1/L is too high), the adsorption force between the molecules of the analyte and the plurality of silicon nanowires 22 is greatly reduced, resulting in a longer separation distance, higher cost, and longer measurement time. On the other hand, as shown in FIG. 2, the ratio L2/L between the length L2 of the side wall 25, which is not covered by the metal layer 30, and the length L of the silicon nanowire 22 can be from about 0.2 to 0.8 (such as from about 0.26 to 0.7). According to embodiments of the disclosure, the Raman detecting chip for thin layer chromatography of the disclosure can further include a modification layer 40 disposed on the side wall 25 which is not covered by the metal layer 30, as shown in FIG. 3. The modification layer 40 can be a material which increases or reduces the adsorption force between the molecules of the analyte and the silicon nanowire. For example, the modification layer 40 can be formed on the side wall 25, which is not covered by the metal layer 30, of the silicon nanowire 22, and the modification layer 40 can be a silicon oxide layer, silicon nitride layer, aluminum oxide layer, or a functional modification material which adjusts the polarity of the silicon nanowire.

Figure 4:
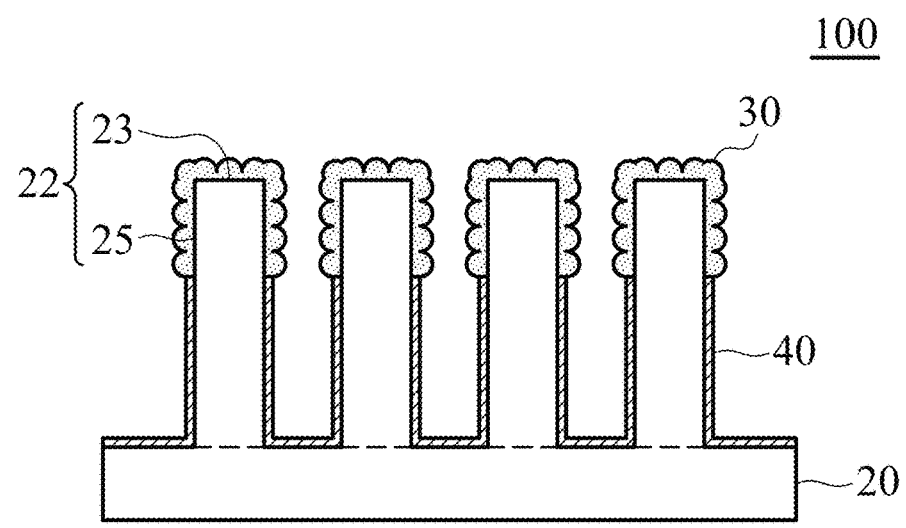

According to embodiments of the disclosure, the modification layer 40 can be formed on the side wall 25 which is not covered by the metal layer 30, and further formed on the surface of the planar portion 20 of the silicon substrate 10 (i.e. the surface, which is not covered by the silicon nanowires 22, of the planar portion 20), as shown in FIG. 4.

Figure 5:
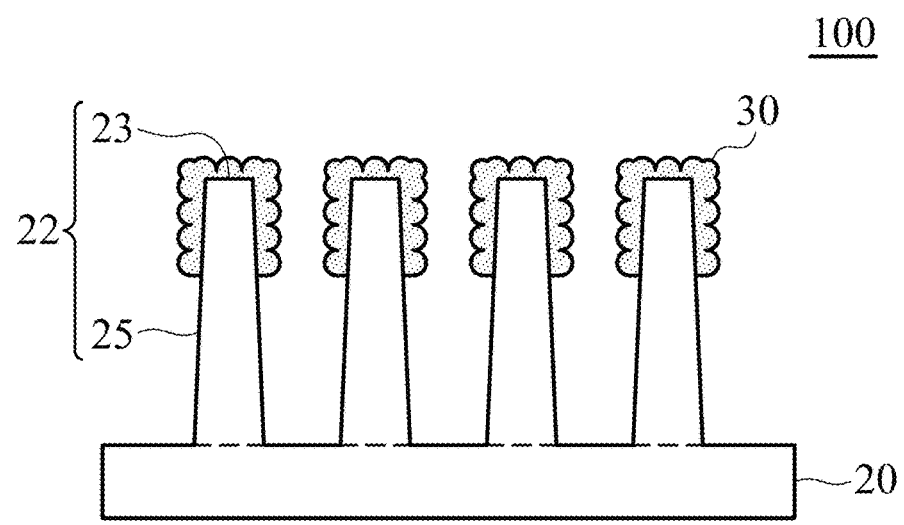

According to some embodiments of the disclosure, the side wall 25 of the nanowire 22 can be a slanted side wall, as shown in FIG. 5. Namely, the side wall 25 of the nanowire 22 is not perpendicular to the planar portion 20. The silicon nanowires 22 are apt to be substantially perpendicular to the planar portion 20 of the silicon substrate 10 when the side wall 25 of the nanowire 22 is a slanted side wall.

Figure 6A:
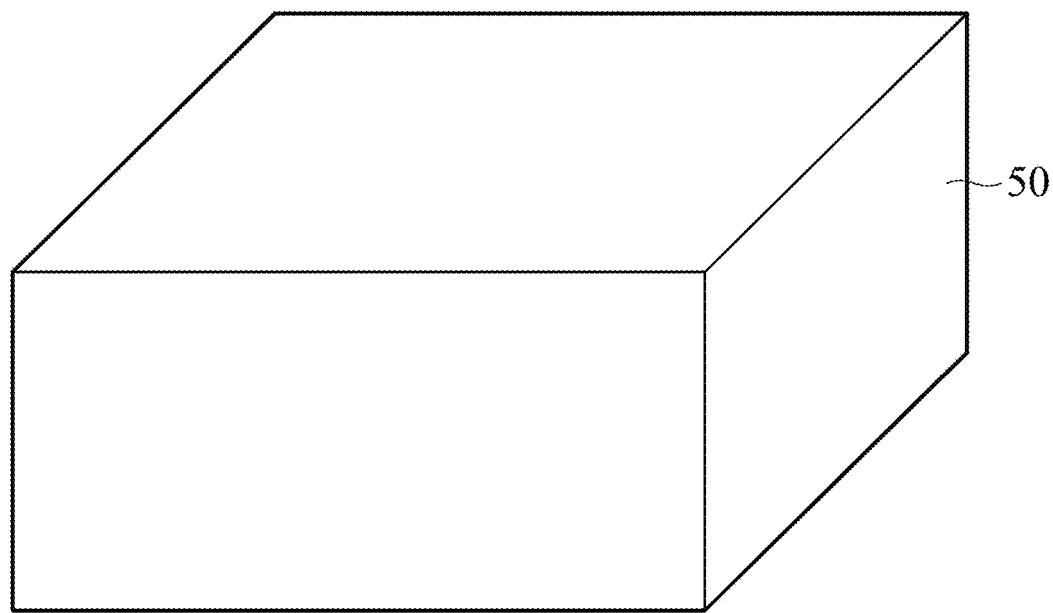
FIGS. 6A-6D are schematic views showing a fabrication process of the silicon substrate according to embodiments of the disclosure.
Figure 6B:
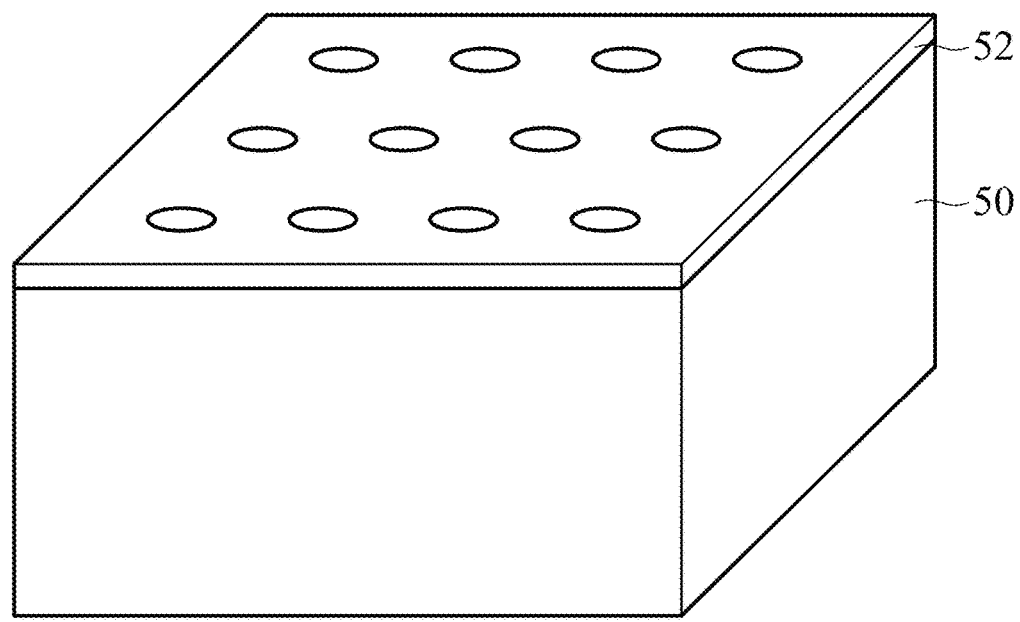
Figure 6C:
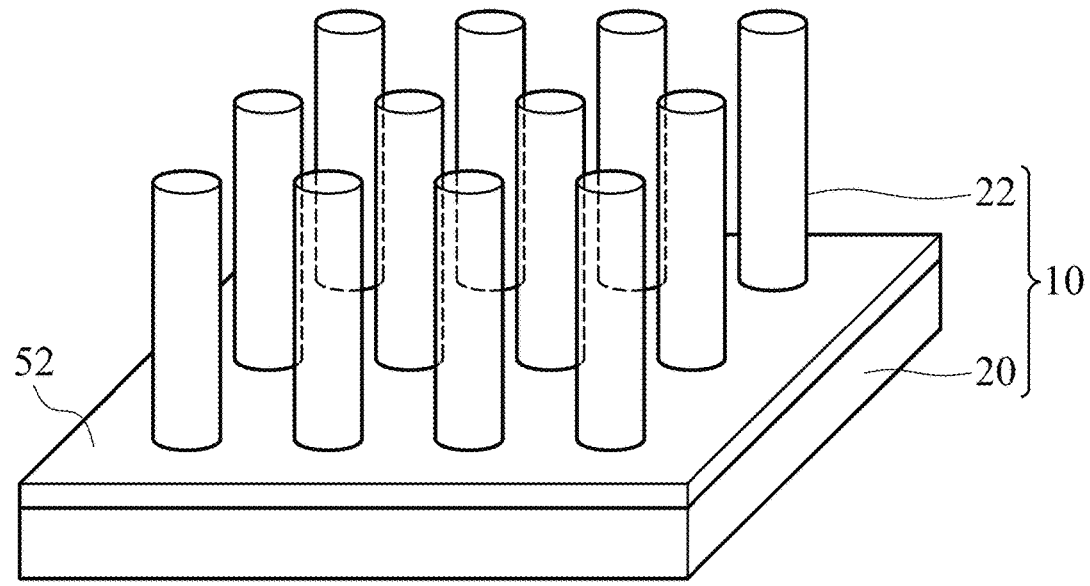
Figure 6D:
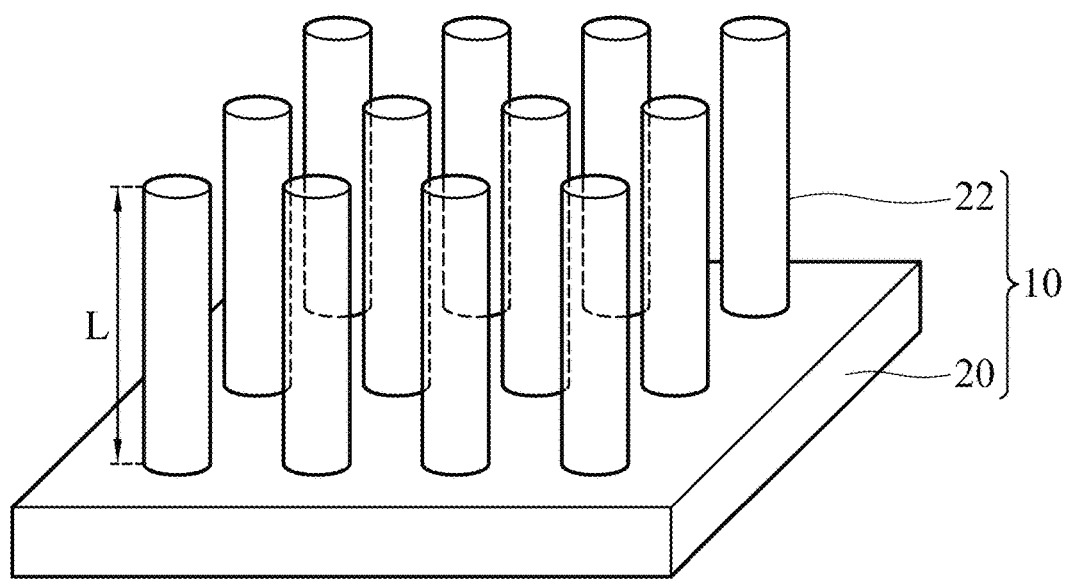

According to embodiments of the disclosure, the fabrication process of the Raman detecting chip for thin layer chromatography of the disclosure can include the following steps. First, a silicon chip 50 (such as a single-crystalline silicon chip) with a specific size is provided, as shown in FIG. 6A. For example, the single-crystalline silicon chip 50 can have a length from about 20 mm to 25 mm, a width from about 10 mm to 15 mm, and a thickness from about 500 μm to 1 mm. Next, the single-crystalline silicon chip 50 is immersed in a first solution (including silver nitrate ($AgNO_3$) and hydrofluoric acid (HF)) for a first time period (such as about 5-10 seconds), and thus a network-shaped silver nano-scale pattern 52 is formed on the top surface 51 of the single-crystalline silicon chip 50, as shown in FIG. 6B. Next, the top surface 51 of the single-crystalline silicon chip 50 is separated from the first solution. Next, the top surface 51 of the single-crystalline silicon chip 50 (having a network-shaped silver nano-scale pattern 52) is immersed in a second solution (including hydrogen peroxide ($H_2O_2$) and hydrofluoric acid (HF)) for a second time period (such as about 1-40 minutes), such that the single-crystalline silicon chip 50 is subjected to a metal assisted chemical etching (MACE) process. In the metal assisted chemical etching process, the surface, which is covered by the network-shaped silver nano-scale pattern 52, of the single-crystalline silicon chip 50 is etched downward, as shown in FIG. 6C. Next, the network-shaped silver nano-scale pattern 52 is removed, thereby obtaining the silicon substrate 10 consisting of the planar portion 20 and the plurality of nanowires 22 as shown in FIG. 6D. In addition, the length L of the nanowire 22 can be controlled by increasing or reducing the time period of the metal assisted chemical etching process. For example, the length L of the nanowire 22 and the time period of the metal assisted chemical etching process are in direct proportion. Finally, the silicon substrate 10 is separated from the second solution, and then the silicon substrate 10 is immersed in a third solution for a third time period (such as about 30-240 seconds) such that the metal layer (a silver layer) is formed to cover the top surface 23 of the silicon nanowire 22 and further extend towards the side wall 25 to cover a part of the side wall 25 of the silicon nanowire 22. Therefore, the Raman detecting chip for thin layer chromatography 100 as shown in FIG. 1 is obtained. Herein, the length L1 of the silicon nanowire 22 covered by the metal layer 30 can be controlled by increasing or reducing the third period of time. For example, the length L1 of the silicon nanowire 22 covered by the metal layer 30 and the third period of time are in direct proportion.

Figure 7A:
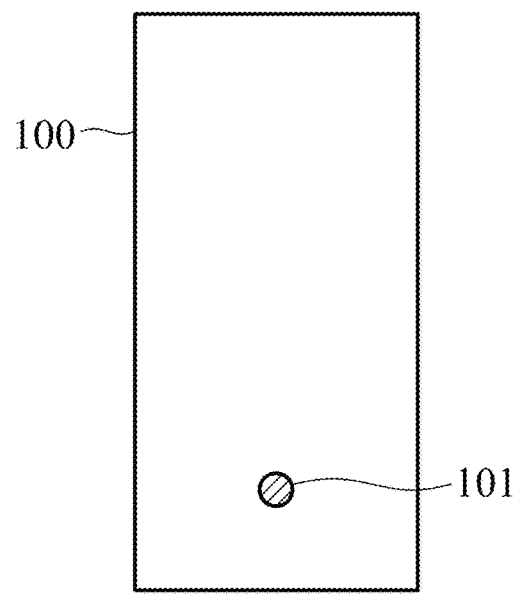
FIGS. 7A and 7B are schematic views showing a thin layer chromatography process employing the Raman detecting chip for thin layer chromatography according to an embodiment of the disclosure.
Figure 7B:
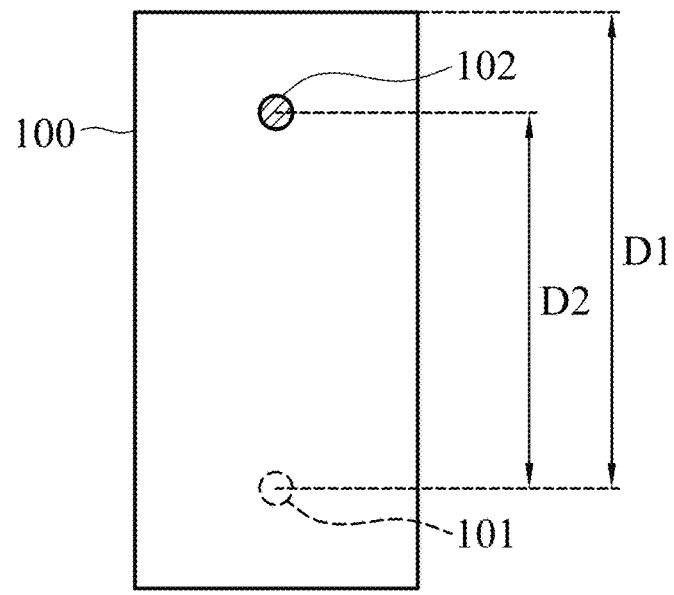

According to embodiments of the disclosure, the disclosure also provides a method for separating and detecting an analyte. The method includes the following steps. First, a Raman detecting chip for thin layer chromatography of the disclosure is provided. Next, a sample is provided, wherein the sample includes a solvent and at least one compound. Herein, the solvent can be a solvent which can be used to dissolve the compound. Next, the sample is spotted onto the Raman detecting chip for thin layer chromatography 100 to form a sample spot 101, as shown in FIG. 7A. Next, the compound of the sample is separated by thin layer chromatography process. Thus, at least one analysis spot 102 can be formed on the Raman detecting chip 100, as shown in FIG. 7B.

Finally, the analysis spot is analyzed via surface enhanced Raman scattering spectroscopy. In particular, the distance D1 is the distance that a developing solution travels up the Raman detecting chip 100, and the distance D2 is the distance between the analysis spot 102 and the sample spot 101. The retention factor (Rf) value may represent the quotient of D2 over D1 (i.e. Rf value is D2/D1). In the thin layer chromatography process, the Raman detecting chip for thin layer chromatography 100 is used as a stationary phase, and a developing solution (liquid) is used as a mobile phase. The developing solution is not limited and may be chosen according to the discretion of one skilled in the art. For example, the developing solution can include, but is not limited to, dichloromethane (DCM), methanol, ethyl ether, ethyl acetate (EA), n-hexane, acetone, chloroform, toluene, water, or a combination thereof.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

First, a single-crystalline silicon chip (15 mm×25 mm) was provided. Next, the single-crystalline silicon chip was immersed in a solution including silver nitrate ($AgNO_3$) and hydrofluoric acid (HF)) for a first time period (about 10 seconds). In particular, a network-shaped silver pattern was formed on one surface of the single-crystalline silicon chip. Next, the single-crystalline silicon chip was separated from the solution, and then the single-crystalline silicon chip was immersed in a solution including hydrogen peroxide ($H_2O_2$) and hydrofluoric acid (HF) for a second time period (about 4 minutes), such that the single-crystalline silicon chip was subjected to a metal assisted chemical etching (MACE) process. After removing the network-shaped silver pattern, a silicon substrate having a plurality of silicon nanowires was obtained, wherein the average length L of the silicon nanowires was of about 1 μm. Next, the silicon substrate was immersed in a solution including silver nitrate ($AgNO_3$) for a third time period (about 120 seconds), and then a silver particle layer was formed to cover the top surface and a part of the side wall of the silicon nanowire. Therefore, Raman detecting chip (1) was obtained, wherein the ratio L1/L between the length L1 of the side wall covered by the silver particle layer and the length L of the silicon nanowire was about 0.74.

Example 2

Example 2 was performed in the same manner as in Example 1 except that the second time period was increased from 4 to 8 minutes, obtaining Raman detecting chip (2). In particular, the average length L of the silicon nanowires of Raman detecting chip (2) was of about 2 μm, and the ratio L1/L was of about 0.6.

Example 3

Example 3 was performed in the same manner as in Example 1 except that the second time period was increased from 4 to 20 minutes, obtaining Raman detecting chip (3). In particular, the average length L of the silicon nanowires of Raman detecting chip (3) was of about 5 μm, and the ratio L1/L was of about 0.46.

Example 4

Figure 8:
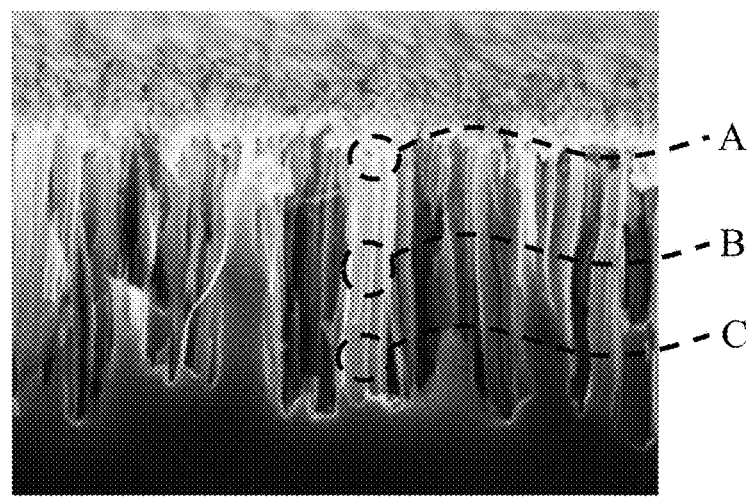
FIG. 8 is scanning electron microscope (SEM) photograph of a cross-sectional structure of the Raman detecting chip (4) as disclosed in Example 4.

Example 4 was performed in the same manner as in Example 1 except that the second time period was increased from 4 to 40 minutes, obtaining Raman detecting chip (4). In particular, the average length L of the silicon nanowires of Raman detecting chip (4) was of about 10 μm, and the ratio L1/L was of about 0.4. FIG. 8 is a scanning electron microscope (SEM) photograph of a cross-sectional structure of the Raman detecting chip (4) as disclosed in Example 4. The ratio of silver to silicon of regions A, B, and C shown in FIG. 8 were measured by energy dispersive spectroscopy (EDS), and the results are shown in Table 1.

TABLE 1

| | ratio of silver to silicon (Ag/Si) |
|---|---|
| region A | 0.123 |
| region B | 0.118 |
| region C | 0.0012 |

As shown in Table 1, the silver particle layer is formed on the upper part of the silicon nanowire and is not formed on the lower part of the silicon nanowire.

Example 5

Example 5 was performed in the same manner as in Example 1 except that the second time period was increased from 4 to 60 minutes, obtaining Raman detecting chip (5). In particular, the average length L of the silicon nanowires of Raman detecting chip (5) was of about 15 µm, and the ratio L1/L was of about 0.37.

Example 6

Example 6 was performed in the same manner as in Example 1 except that the second time period was increased from 4 to 80 minutes, obtaining Raman detecting chip (6). In particular, the average length L of the silicon nanowires of Raman detecting chip (6) was of about 20 µm, and the ratio L1/L was of about 0.3.

Detection and Separation of Melamine by Means of Raman Detecting Chips

Example 7

Figure 9:
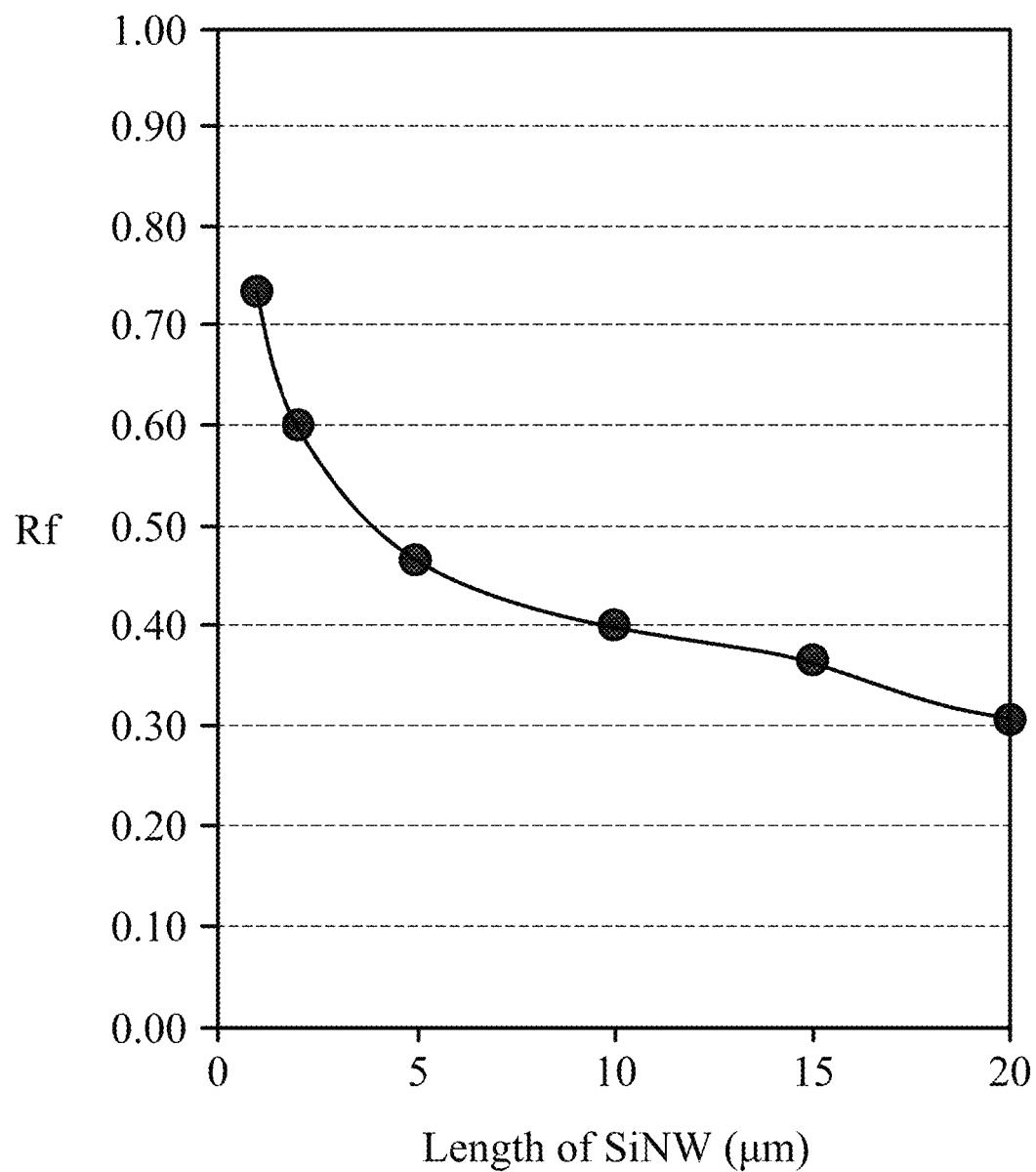
FIG. 9 is a graph plotting silicon nanowire length against retention factor (Rf) value in Examples 1-6.

First, a milk added to 50 ppm of melamine was provided and served as a sample. Next, the sample was applied to Raman detecting chips (1)-(6) with the Camag Linomat 5 sample applicator via air pressure. Next, Raman detecting chips (1)-(6) were disposed in developing tanks respectively, and the sample was developed with methanol serving as a developing solution. After developing, the Rf value of strongest melamine signal of Raman detecting chips (1)-(6) was determined by surface enhanced Raman scattering spectroscopy, and the results are shown in FIG. 9. In particular, the Raman detecting chip have several analysis spots arranged in developing direction, and each two adjacent analysis spots are separated by an interval of 1 mm.

As shown in FIG. 9, when the length L of the silicon nanowire of the Raman detecting chip is less than about 5 µm (such as 1 µm, or 2 µm), the adsorption force between the molecules of the analyte and the plurality of silicon nanowire is greatly reduced, resulting in a longer separation distance (relatively high Rf value), higher cost, and longer measurement time. When the length L of the silicon nanowire of the Raman detecting chip is greater than about 15 µm (such as 20 µm), the adsorption force between the molecules of the analyte and the plurality of silicon nanowire is greatly increased, resulting in the analyte not being apt to move with the developing solution, meaning that the separation distance is reduced (relatively low Rf value) and melamine is not identified and isolated. In addition, according to the results of Example 7, the Raman scattering signal strength of melamine is reduced when the separation distance is relatively low or high.

Example 8

Figure 10:
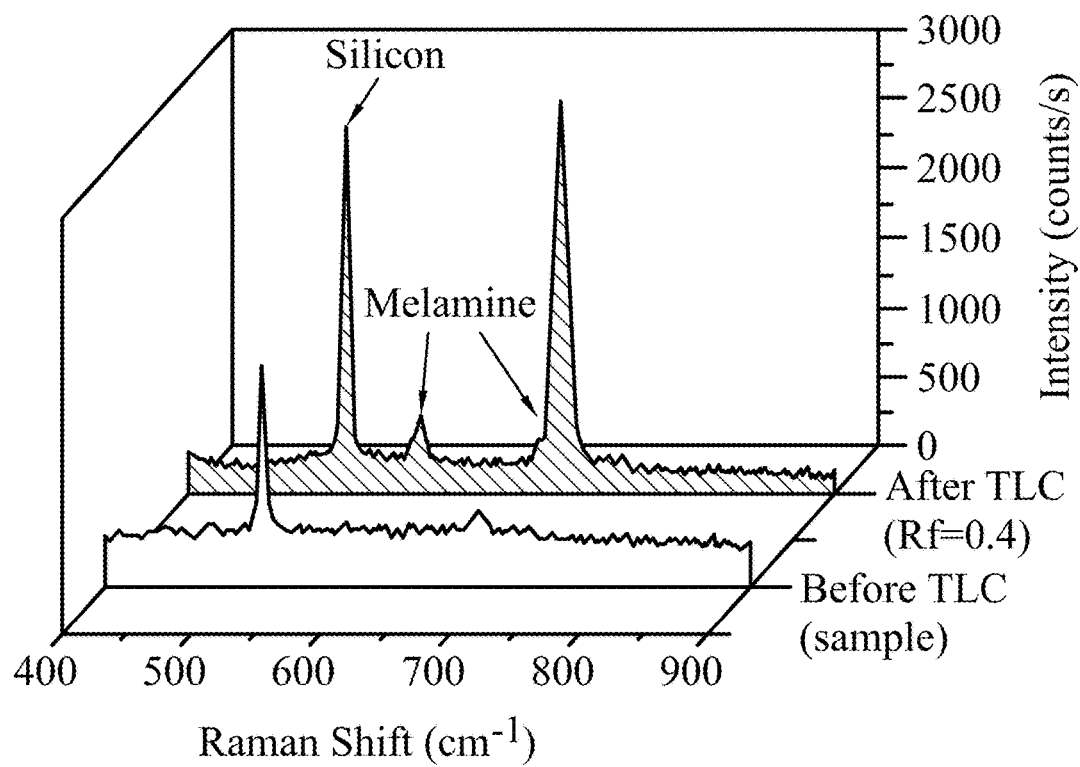
FIG. 10 is a Raman spectrum for detecting melamine surface enhanced Raman scattering spectroscopy employing the Raman detecting chip (4) as disclosed in Example 9.

First, a milk added to 30 ppm of melamine was provided and served as a sample. Next, the sample was applied to Raman detecting chip (4) with the Camag Linomat 5 sample applicator via air pressure. Next, the sample point was analyzed via surface enhanced Raman scattering spectroscopy, and the result is shown in FIG. 10. Next, Raman detecting chip (4) is disposed in developing tank, and the sample was developed with methanol serving as a developing solution. After developing, the Rf value of strongest melamine signal of Raman detecting chip (4) was determined by surface enhanced Raman scattering spectroscopy, and the results are shown in FIG. 10. In particular, the Raman detecting chip has several analysis spots arranged in the developing direction, and each two adjacent analysis spots are separated by an interval of 1 mm. As shown in FIG. 10, in comparison with the sample point (before developing), the Raman scattering signal strength of melamine in the analysis spot with an Rf value of 0.4 is ten times more than the Raman scattering signal strength of melamine in the sample point. It means that the melamine (small molecule) can be separated from the protein (large molecule) after developing and the interference caused by the protein occupying the detection area, resulting in enhancing the Raman scattering signal strength of melamine.

Example 9

Example 9 was performed in the same manner as in Example 8 except that the concentration of melamine was reduced from 30 to 5 ppm. In comparison with the sample point (before developing), the strongest Raman scattering signal strength of melamine in the analysis spot is five times more than the Raman scattering signal strength of melamine in the sample point. As a result, the Raman detecting chip of the disclosure can efficiently eliminate background interference and increase detectability even though the concentration of melamine was low.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A Raman detecting chip for thin layer chromatography, comprising:
   a silicon substrate comprising
   a flat portion;
   a plurality of silicon nanowires disposed on the flat portion, wherein each silicon nanowire has a top surface and a sidewall; and
   a metal layer covering the top surface and at least a part of the sidewall of the silicon nanowire, wherein the silicon nanowire has a length L from 5 µm to 15 µm, wherein the metal layer disposed on the top surface of the silicon nanowire extends to the side wall of the silicon nanowire, such that the metal layer covers a part of the side wall of the silicon nanowire, and the ratio between the length L1 of the side wall covered by the metal layer and the length L of the silicon nanowire is from 0.2 to 0.8.

2. The Raman detecting chip for thin layer chromatography as claimed in claim 1, wherein the metal layer consists of a plurality of metal particles.

3. The Raman detecting chip for thin layer chromatography as claimed in claim 1, wherein a material of the metal particles is silver, gold, aluminum, copper, tin, titanium, barium, platinum, cobalt, or a combination thereof.

4. The Raman detecting chip for thin layer chromatography as claimed in claim 1, wherein the top surface of the silicon nanowire has a diameter from 50 nm to 200 nm.

5. The Raman detecting chip for thin layer chromatography as claimed in claim 1, wherein distance between two adjacent silicon nanowires is from 50 nm to 200 nm.

6. The Raman detecting chip for thin layer chromatography as claimed in claim 1, wherein the metal layer has a thickness from 20 nm to 100 nm.

7. The Raman detecting chip for thin layer chromatography as claimed in claim 1, wherein the ratio between the length L1 of the side wall covered by the metal layer and the length L of the silicon nanowire is from 0.3 to 0.74.

8. The Raman detecting chip for thin layer chromatography as claimed in claim 1, further comprising:

a modification layer disposed on the side wall of the silicon nanowire which is not covered by the metal layer.

9. The Raman detecting chip for thin layer chromatography as claimed in claim 8, wherein the modification layer is a silicon oxide, silicon nitride, aluminum oxide, or a functional modification material which adjusts polarity of the silicon nanowire.

10. The Raman detecting chip for thin layer chromatography as claimed in claim 1, wherein the side wall of the silicon nanowire is a slanted sidewall.

11. A method for separating and detecting an analyte, comprising:
  providing the Raman detecting chip for thin layer chromatography as claimed in claim 1;
  providing a sample, wherein the sample comprises a solvent and at least one compound;
  spotting the sample on the Raman detecting chip for thin layer chromatography as claimed in claim 1;
  separating the sample by a thin layer chromatography process to obtain at least one analysis spot; and
  analyzing the analysis spot via surface enhanced Raman scattering spectroscopy.

\* \* \* \* \*